(12) United States Patent
Qiu

(10) Patent No.: US 8,883,161 B2
(45) Date of Patent: Nov. 11, 2014

(54) FUSION POLYPEPTIDE AGAINST EB VIRUS-INDUCED TUMOR AND COLICIN IA MUTANT

(75) Inventor: Xiaoqing Qiu, Chengdu (CN)

(73) Assignee: Protein Design Lab, Ltd., Beijing (CN)

( * ) Notice: Subject to any disclaimer, the term of this patent is extended or adjusted under 35 U.S.C. 154(b) by 0 days.

(21) Appl. No.: 13/516,605

(22) PCT Filed: Feb. 26, 2010

(86) PCT No.: PCT/CN2010/070762
§ 371 (c)(1),
(2), (4) Date: Jun. 15, 2012

(87) PCT Pub. No.: WO2011/072501
PCT Pub. Date: Jun. 23, 2011

(65) Prior Publication Data
US 2013/0066051 A1 Mar. 14, 2013

(30) Foreign Application Priority Data

Dec. 17, 2009 (CN) .......................... 2009 1 0242838

(51) Int. Cl.
| | |
|---|---|
| C07K 5/00 | (2006.01) |
| A61K 39/395 | (2006.01) |
| C07K 16/08 | (2006.01) |
| C07K 14/245 | (2006.01) |
| C07K 19/00 | (2006.01) |
| C07K 14/005 | (2006.01) |
| A61K 39/00 | (2006.01) |

(52) U.S. Cl.
CPC ............ *C07K 16/085* (2013.01); *C07K 14/245* (2013.01); *C07K 19/00* (2013.01); *C07K 14/005* (2013.01); *A61K 2039/505* (2013.01); *C07K 2319/30* (2013.01); *C12N 2710/16222* (2013.01)
USPC ....... 424/178.1; 530/350; 530/402; 435/69.1; 435/69.7

(58) Field of Classification Search
CPC . C07K 2319/00; A61K 38/00; A61K 38/164; A61K 2039/505; A61K 47/48438; A61K 47/48484; A61K 47/48561
See application file for complete search history.

(56) References Cited

U.S. PATENT DOCUMENTS

| 8,367,066 B2 * | 2/2013 | Qiu | ............................ 424/183.1 |
|---|---|---|---|
| 2006/0193867 A1 | 8/2006 | Qiu | |
| 2006/0233813 A1 | 10/2006 | Qiu | |

FOREIGN PATENT DOCUMENTS

| CN | 1341604 A | 3/2002 |
|---|---|---|
| CN | 1641024 A | 7/2005 |
| CN | 101633699 A | 1/2010 |
| CN | 101643501 A | 2/2010 |
| WO | 2007/083175 A1 | 7/2007 |

OTHER PUBLICATIONS

X. Qiu et al. "Major Transmembrane Movement Associated with Colicin Ia Channel Gating" J. Gen. Physiology, 107: pp. 313-328 (1996).
X. Qiu et al. "Small antibody mimetics comprising two complementarity-determining regions and a framework region for tumor targeting" Nature Biotechnology, vol. 25, No. 8. (Aug. 5, 2007), pp. 921-929.
Supplementary European Search Report dated Nov. 4, 2013 as received in Application No. 10836940.6.
Schramm et al., "Nucleotide Sequence of the Colicin B Activity Gene cba: Consensus Pentapeptide among TonB-Dependent Colicins and Receptors", Journal of Bacteriology, vol. 169, Issue 7, Jul. 1987, pp. 3350-3357.
Riley., "Molecular Mechanisms of Colicin Evolution", Molecular Evolution of Colicins, vol. 10, Issue 6, 1993, pp. 1380-1395.
Geli et al., Recognition of the colicin A N-terminal epitope 1C11 in vitro and in vivo in *Escherichia coli* by its cognate monoclonal antibody, FEMS Microbiology Letters, vol. 109, Issue 2-3, May 15, 1993, pp. 335-342.
Cavard et al., "A Molecular, Genetic and Immunological Approach to the Functioning of Colicin A, a Pore-forming Protein", Journal of Molecular Biology, vol. 187, Issue 3, Feb. 5, 1986, pp. 449-459.
Ladner., "Antibodies cut down to size", Nature Biotechnology, vol. 25, Issue 8, Aug. 2007, pp. 875-877.
Zhen et al., "Development of a novel small antibody that retains specificity for tumor targeting", Journal of Experimental & Clinical Cancer Research, vol. 28, Issue 1, Apr. 30, 2009, pp. 1-10.

* cited by examiner

*Primary Examiner* — Michelle S Horning
(74) *Attorney, Agent, or Firm* — Maschoff Brennan

(57) ABSTRACT

The present invention provides a fusion polypeptide against EB virus-induced tumor, which comprises an antibody or a mimetic antibody against EB virus and an ion channel forming colicin selected form E1, Ia, Ib, A, B, N and their mutants. The present invention also provides a colicin Ia mutant, which comprises mutations of G11A, H22G, A26G, V31L, and H40D. The present invention also provides a gene, vector, preparation method and use of the fusion polypeptide, and provides a gene and use of the mutant.

10 Claims, 4 Drawing Sheets

(3 of 4 Drawing Sheet(s) Filed in Color)

US 8,883,161 B2

FUSION POLYPEPTIDE AGAINST EB VIRUS-INDUCED TUMOR AND COLICIN IA MUTANT

FIELD OF THE INVENTION

The present invention relates to the filed of anti-tumor agents, and more specifically, to a novel polypeptide against tumor caused by EB virus and use and preparation method thereof.

RELATED ART

In the area of antibiotics research, studies have been directed towards development of new antibiotics which simulate the inter-killing mechanism among homogeneous heterologous strains. There are a lot of bacterial toxins in the nature which kill cells by forming ion channels on the cellular membrane of bacteria directly. The model example of such toxin is colicin, a bacteria toxin secreted by *E. coli*. Colicin Ia was found by Jacob in 1952, since then, via the hard work of generations, Qiu et al. (Major transmembrane movement associated with colicin Ia channel gating. J. Gen. Physiology, 107:313-328 (1996)) finally revealed the transmembrane spatial structure of colicin Ia when the ion channels formed in artificia lipid bilayer membranes is open or closed, which provides a fundamental basis for the design and preparation of new antibiotics at molecular level. Subsequently, there are polypeptide molecules made by the connection of colicin polypeptide with signal peptide such as pheromones of *Streptococcus albus* or *Staphylococcus*, which target the colicin to the cell membrane of bacteria interested and kill the cell due to the leak of cellular contents through the transmembrane ion channels formed.

Malignant tumor poses a great threat to human health. Seven million people die from malignant tumor every year in the world, one sixth of which are in China. Malignant tumor is now the second leading cause of death in our country. Since the etiology, pathogenesis and clinical manifestation of malignant tumor are not clearly elucidated, prevention and treatment is not effective. Anti-tumor agents are important in the treatment of tumor. Although they achieve therapeutic effect to some tumor, there remains some disadvantage, such as insufficient tumor selectivity, immunological suppression, adverse reaction, drug resistance, etc.

The surface of cells of Burkitt's lymphoma, Hodgkin's lymphoma and nasopharyngeal carcinoma caused by Epstein-Barr (EB) Virus bears a specific surface antigen of EB virus. Therefore, EB virus surface antigen can be regarded as a specific marker of such tumor cells. For the agents against the tumor caused by EB virus, the invention with the china patent No. ZL200410081446.8 discloses an anti-tumor polypeptide formed by the conjugation of colicin and antibody mimetics which recognize EB virus surface antigen. The anti-tumor polypeptide can specifically kill the cancer cells caused by EB virus in the body, has no harm to normal cells, the killing ability of which is several times over other anti-tumor agents, and overcomes the problems such as tumor selectivity, drug resistance, impairment of normal tissue when the cancer cells are killed. Xiao-Qing Qiu et al. (Xiao-Qing Qiu et al., 2007, Small antibody mimetics comprising two complementarity-determining regions and a framework region for tumor targeting, *Nature Biotechnology* 25, 921-929, 1 Aug. 2007) compare the killing effect of anti-tumor polypeptides constructed by a series of antibody mimetics and colicin, and find that anti-tumor polypeptides constructed by antibody mimetics of $V_H$CDR1-$V_H$FR$_2$-$V_L$CDR3 and $V_L$CDR1-$V_H$FR$_2$-$V_H$CDR3 with colicin have superior killing ability. This work provides more candidate antibody mimetics for the preparation of polypeptides against tumor caused by EB virus.

However, for the anti-tumor polypeptide described above, since the hydrophobic terminal of colicin has some amino acid residues which may include hypersensitivity, the medicine comprising polypeptide of colicin is possible to elicit abnormal immune responses in vivo more easily. It's reported that metabolic mechanism of many cancer patient is abnormal due to the disturbance from cancer cells, they are easy to suffer an allergic response to medicine of polypeptides, thus can not be treated by such medicine. Therefore, it is necessary to improve colicin polypeptide in order to obtain an anti-cancer medicine which is safer and suitable for more patients.

SUMMARY OF THE INVENTION

Base on the disadvantage of prior art stated above, the present invention provides a novel polypeptide against tumor caused by EB virus and use and preparation method thereof, thus provides a medicine for the treatment of tumor caused by EB virus which has high killing ability, high specificity, and low possibility of allergy.

A novel polypeptide against tumor caused by EB virus, which is formed by operable linkage of a mutant polypeptide of colicin which can form ion channels with a polypeptide of anti-EB virus antibody or a polypeptide of anti-EB virus antibody mimetics, the mutant polypeptide of colicin which can form ion channels is obtain by mutation of amino acid residues of G11A, H22G, A26G, V31L, and H40D to peptide chain of wild-type colicin E1, Ia, Ib, A, B, N or aqueous channel domain thereof, the amino acid sequence of the polypeptide of anti-EB virus antibody is the same as the polypeptide of monoclonal antibody secreted by hybridoma of ATCC HB-168.

The polypeptide of antibody mimetics is a connected peptide of CDR1 region of heavy chain, linking peptide segment of CDR1-CDR2 of heavy chain and CDR3 of light chain of anti-EB virus antibody.

The mutant polypeptide of colicin which can form ion channels is obtained by mutation of wild-type colicin Ia.

The novel polypeptide against tumor caused by EB virus has the amino acid sequence shown in SEQ ID NO. 29.

A gene encoding the novel polypeptide against tumor caused by EB virus.

The gene, which has the nucleotide sequence shown in SEQ ID NO. 30.

A recombination plasmid comprising said gene.

A preparation method for the novel polypeptide against tumor caused by EB virus, comprising steps of: transforming said recombination plasmid into an expression system for expression, and isolating the polypeptide expressed.

Use of said novel polypeptide against tumor caused by EB virus in preparation of a medicament for the treatment and prevention of tumor caused by EB virus.

A mutant polypeptide of colicin Ia, its amino acid sequence is shown in SEQ ID NO. 24.

A gene encoding a mutant polypeptide of colicin Ia.

Use of said gene in preparation of peptide medicament, operably linking said gene with a gene which induces the peptide, cloning into an expression vector, then transforming the expression vector into an expression system, and isolating the polypeptide expressed.

The invention provides a novel polypeptide against tumor caused by EB virus, which is formed by a mutant polypeptide of colicin which can form ion channels with a polypeptide of anti-EB virus antibody or a polypeptide of anti-EB virus antibody mimetics. Since there are some amino acid residues in the wild-type colicin polypeptide molecule which may include hypersensitivity, in the polypeptide molecule of colicin which can form ion channel construct, the invention selectively mutates amino acid residues in the hydrophobic region which may elicit allergic response easily. For example, in a preferred embodiment of the invention, the mutant sites of polypeptide of colicin Ia are: G11A, H22G, A26G, V31L and H40D. In mice immunized with injection of a polypeptide of colicin Ia or a polypeptide of mutant Ia respectively, the experimental data shows that serum titer produced by the mice injected with the polypeptide of mutant Ia is several orders of magnitude lower than the former, that is to say, the level of immune response is lower, demonstrating that the mutant polypeptide reduces the possibility of allergy, while the mutant polypeptide retains the function of forming ion channels in cell membrane. The experiment showed that the killing ability of the recombinant polypeptide of the invention is not affected, which means that the mutant amino acid residues do not affect the function of forming ion channels for colicin. In the novel polypeptide against tumor caused by EB virus provided by the invention, via the recognition of the polypeptide of anti-EB virus antibody or the polypeptide of anti-EB virus antibody mimetics to the surface antigen of tumor cells caused by the EB virus, the mutant polypeptide of colicin is targeted to the membrane of target cells, the hydrophobic region of transmembrane ion channel domain of the mutant polypeptide of colicin is inserted to the cell membrane of tumor cells, and forms an ion channel, therefore the tumor cells die from the leak of cellular contents. The amino acid sequence of polypeptide of anti-EB virus antibody completely refers to the amino acid sequence of the polypeptide of antibody secreted by hybridoma of ATCC HB-168.

In an embodiment of the invention, an anti-tumor polypeptide of low molecular weight of the invention is preferred, which is obtained by operable linkage of the polypeptide of anti-EB virus antibody mimetics described above with the carboxyl terminus of the mutant polypeptide of colicin. That is to say, such a mimetic polypeptide of low molecular weight comprises a peptide chain of VHCDR1-VHFR2-VLCDR3 which is obtained by the connection of VHCDR1 region, VLCDR3 region, linking peptide segment of VHCDR1-VH-CDR2 and VLCDR3 of light chain of the polypeptide of the anti-EB virus antibody. The amino acid sequence of the novel anti-tumor peptide 1 of antibody mimetics is shown in SEQ ID NO. 25. The antibody mimetics only comprises amino acids less than 30, and has a much lower molecular weight than natural antibody of 150 amino acids. It fulfills the requirement of antigen recognition while reduces the molecular weight of anti-tumor polypeptide substantially, and contributes to the tissue penetration ability of the anti-tumor polypeptide of the present invention.

Another object of the present invention is to provide a gene sequence encoding the anti-tumor polypeptide of the present invention. The gene of the anti-tumor polypeptide of the present invention is formed by the operable linkage of a gene encoding a mutant polypeptide of colicin with a gene encoding a polypeptide of anti-EB virus antibody or a polypeptide of antibody mimetics thereof, wherein the polypeptide of colicin and the gene sequence of the anti-EB virus antibody is known in the art, the gene of mutant polypeptide of colicin is obtained by the following point mutations in the corresponding codons of the gene of colicin polypeptide: G11A, H22G, A26G, V31L and H40D. As a result of the degeneracy of the genetic code, a skilled person in the art may adjust the nucleotide sequence encoding the anti-tumor polypeptide of the present invention without altering the amino acid sequence.

The recombination plasmid of the present invention means that the original vector loaded with gene of wild-type colicin is site-directed mutated in double stranded nucleotide, and inserted by mutant codons in the site of target mutation, thus obtaining a mutant vector comprising the gene of mutant polypeptide of colicin. The same process of the site-directed mutagenesis inserts a gene encoding antibody mimetics of an anti-EB virus antibody into the carboxyl terminus of a gene of the mutant polypeptide of colicin, thus obtaining a recombinant plasmid of the present invention. The original vector pSELECTTM-1 is purchased from Promega Corp., which carries genes of colicin Ia and Immunity protein. The process of site directed mutagenesis follows the instruction of the kit from Strategene Corp. The present invention carries out some site directed mutagenesis to prepare a mutant polypeptide of colicin, wherein five codons are site-directed mutated. Therefore, 5 pairs of primer sequences are designed (SEQ ID No. 1-10). In the example of the present invention, 6 pairs of primer sequences are designed for the gene of antibody mimetics (SEQ ID No. 11-22).

The present invention also provides a method for the preparation of the anti-tumor polypeptide of the present invention, which comprises transforming the recombinant vector obtained above into an engineering bacteria of *E. coli* BL21 (DE3), selecting positive clone, isolating and purifying the protein expressed by the positive clone, thus obtaining the novel polypeptide against tumor caused by EB virus of the present invention.

The novel polypeptide against tumor caused by EB virus provided by the present invention can be used in preparation of a medicament for the treatment and prevention of tumor caused by EB virus. A clinical suitable pharmaceutical composition can be made by adding the polypeptide of novel antibiotics obtain in the present invention into a pharmaceutically acceptable carrier or vehicle or other optional components.

The present invention also provides the amino acid sequence and the gene sequence of the mutant polypeptide of colicin Ia. The mutant polypeptide can be used in the present invention, also can be used in the construction of an antibody polypeptide with other targeting polypeptides. The experimental data of example 3 in the invention proves that the peptide medicament comprising the mutant polypeptide has a low immunogenicity, and that the antibody polypeptide formed by the mutant polypeptide with other targeting polypeptide has a bactericidal ability. The preparation method is routine experimental process in the art.

The novel anti-tumor polypeptide provided by the invention has the advantage of the anti-tumor polypeptide disclosed in the patent No. ZL200410081446.8, i.e., highly specific targeting and safety to normal cells, and not inclined to developing drug resistance. At the same time, the anti-tumor polypeptide of the present invention has been mutated at the amino acid residues which tend to elicit allergic response, the immunogenicity of the anti-tumor polypeptide comprising such mutant polypeptide is reduced, that is to say, the possibility of allergic reaction is reduced. The use safety and effect of killing tumor of medicament of such polypeptides are improved. This may also be a good example for improvement of other medicament comprising colicin polypeptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(A) Kunming mice intraperitoneally injected with lethal dose of MRSA (ATCC BAA42) are grouped randomly into (1) control group, (2) group of ampicillin, (3) group of polypeptide against *S. aurous* (ZL 01128836.1), (4) group of polypeptide 1 against *S. aurous*.

(B) After 14 days, a new batch of Kunming mice are grouped into a control group and a group of ampicillin. Survived mice from the group of polypeptide against *S. aurous* and the group of polypeptide 1 against *S. aurous* are grouped into a group of polypeptide against *S. aurous* and a group of polypeptide 1 against *S. aurous*, and the experiment is repeated.

(C) After 41 days, a new batch of Kunming mice are grouped into (1) control group, (2) group of levofloxacin, (3) group of ceftriaxone sodium, (4) group of polypeptide against *S. aurous*, and (5) survived mice from the group of polypeptide 1 against *S. aurous* are grouped into a group of polypeptide 2 against *Pseudomonas aeruginosa*, and a group of polypeptide 1 against *Pseudomonas aeruginosa*.

Figure 4:
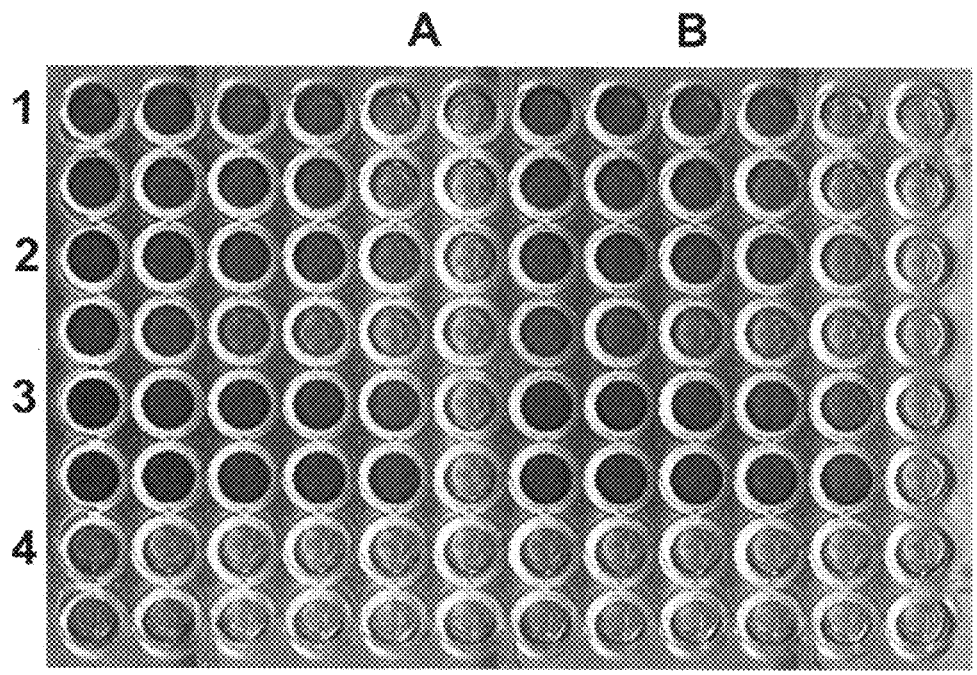

FIG. 4. The experiment 3 of low sensitization effect of the mutant polypeptide of colicin Ia.

(A) the serum of group of polypeptide against *S. aurous*/polypeptide 2 against *Pseudomonas aeruginosa*, titer of 1:50,000;

(B) the serum of group of polypeptide 1 against *S. aurous*/polypeptide 1 against *Pseudomonas aeruginosa*, titer of 1:50,000.

(1) Week 1, (2) Week 2, (3) serum of Week 7, (4) negative control.

Figure 5:
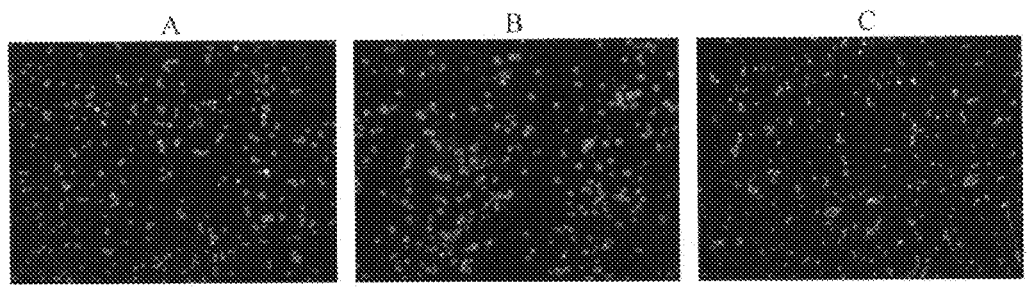

FIG. 5. Comparison of in vitro killing effect of the novel anti-tumor polypeptide to Burkitt's lymphoma caused by EB virus.

(A) control group, (B) novel anti-tumor polypeptide 1 treated group, (C) novel anti-tumor polypeptide 2 treated group.

Figure 6:
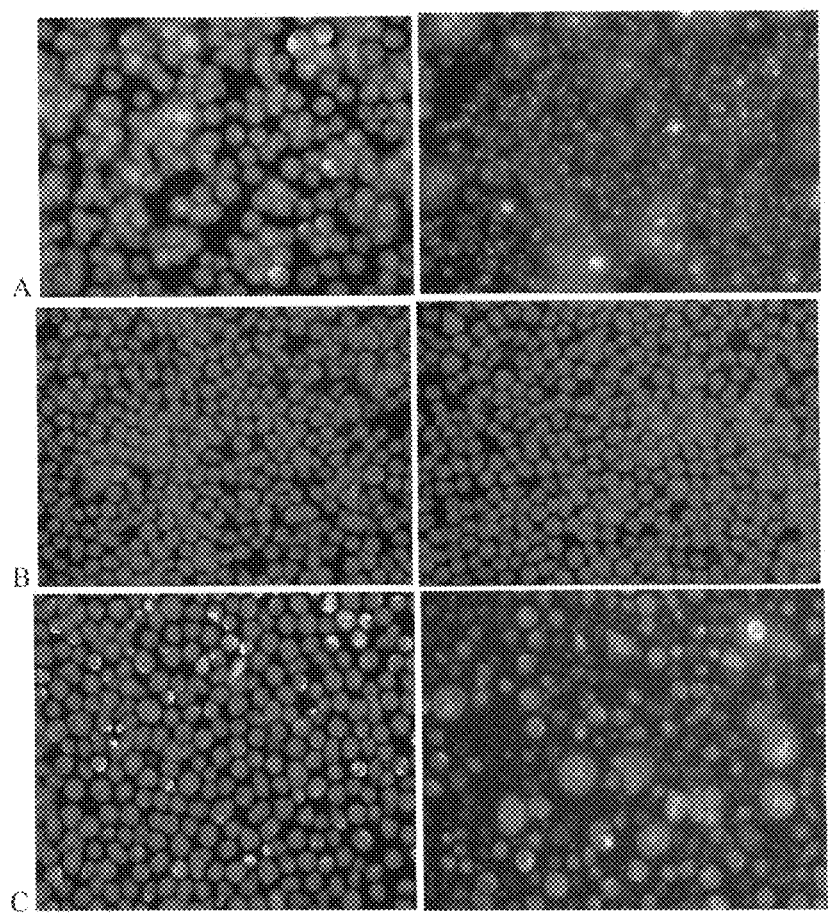

FIG. 6. In vitro killing effect of the novel anti-tumor polypeptide to cells of Burkitt's lymphoma caused by EB virus and other tumor cells.

(A) EBV positive cells of Burkitt's lymphoma, (B) EBV negative cells of Burkitt's lymphoma, (C) EBV positive cells of malignant lymphosarcoma from patient of AIDS.

(1) control group, (2) novel anti-tumor polypeptide 1 treated group.

Figure 7:
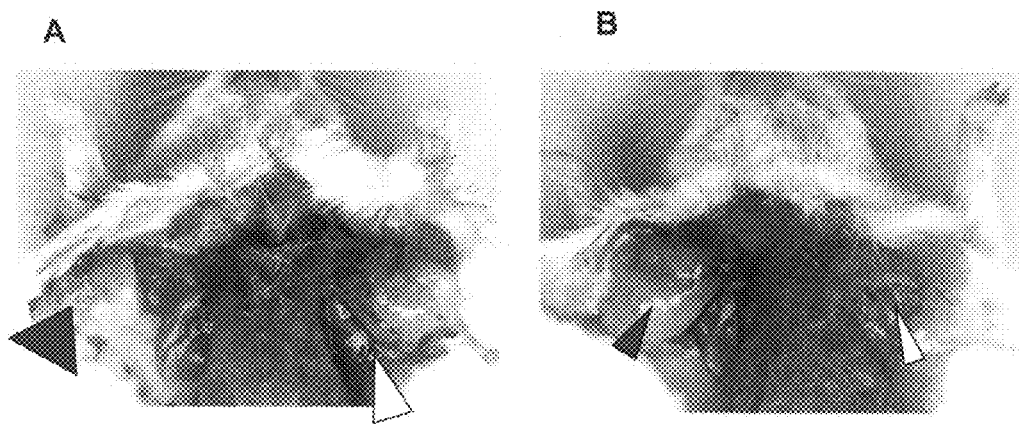

FIG. 7. Killing effect of the novel anti-tumor polypeptide to solid tumor grown from naked mice planted with cells of Burkitt's lymphoma caused by EB virus.

(A) control group.

(B) SCID immunodeficient mice from the novel anti-tumor polypeptide 1 treated group are all inoculated with cells of Burkitt's lymphoma into both axillary flanks Arrow on the left, EBV negative lymphosarcoma, arrow on the right, EBV positive lymphosarcoma.

Figure 8:
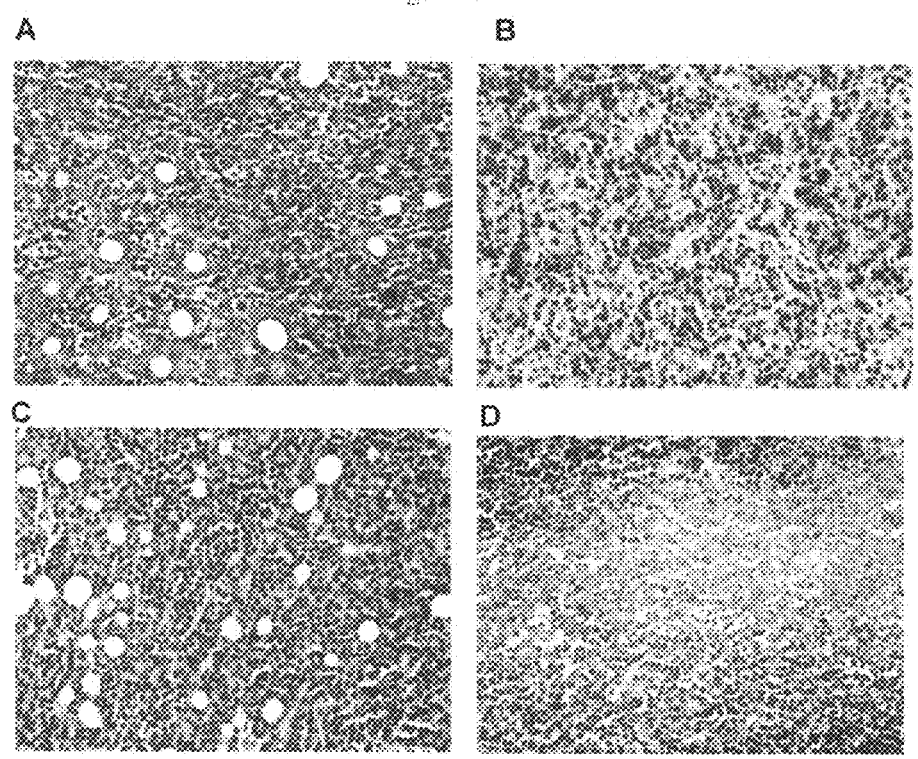

FIG. 8. Killing effect of the novel anti-tumor polypeptide to solid tumor grown from naked mice planted with cells of Burkitt's lymphoma caused by EB virus.

(A) section of EBV negative lymphosarcoma of control mice, (B) section of EBV positive lymphosarcoma of control mice, (C) section of EBV negative lymphosarcoma of novel anti-tumor polypeptide 1 treated mice, (D) section of EBV positive lymphosarcoma of novel anti-tumor polypeptide 1 treated mice.

EMBODIMENTS

The invention will now be describe by describing preferred embodiment of the invention and with reference to the accompany drawings.

The original vector pSELECT™-1 used in the invention is purchased from Promega Corp.

The engineering bacteria of *E. coli* BL21(DE3) is purchased from Novagen Corp.

EXAMPLE 1

Construction of Recombinant Plasmid Comprising Gene Encoding Mutant Colicin Ia

Figure 1:
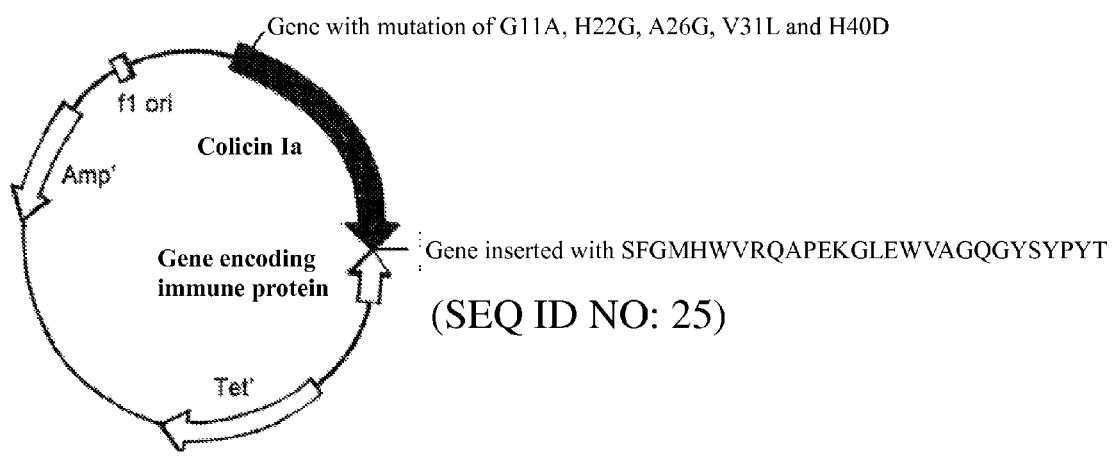
FIG. 1. Schematic illustration of the structure of recombinant plasmid pCHCEB11 which comprises the gene of polypeptide of antibody mimetics of $V_H CDR1$-$V_H FR_2$-$V_L CDR3$ and the gene of the mutant polypeptide of colicin Ia.
Figure 2:
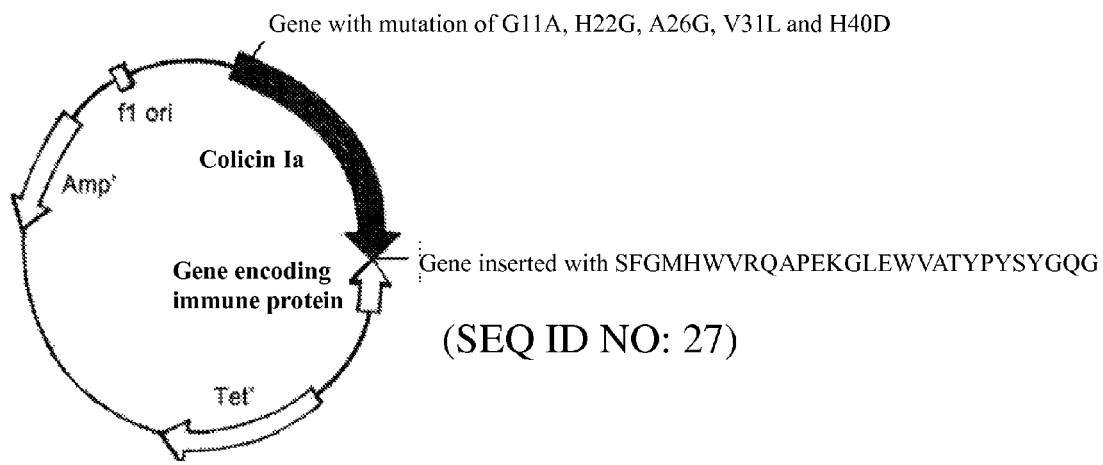
FIG. 2. Schematic illustration of the structure of recombinant plasmid pCHCEB22 which comprises the gene of polypeptide of antibody mimetics of $V_H CDR1$-$V_H FR_2$-(Rev)$V_L CDR3$ and the gene of the mutant polypeptide of colicin Ia.

The original vector is the plasmid pSELECTTM-1 (8.3 kb) (purchased from Promega Corp.) which carries genes of colicin Ia and Immunity protein. Sequences of oligonucleotide primers shown in SEQ ID NOs.1-10 which encode mutant amino acids is operably linked to the gene of wild-type colicin Ia respectively by a double-strand oligonucleotide Site-Directed Mutagenesis technology (QuickChange™ Kit, Strategene Corp.), obtaining a gene shown in SEQ ID NO.23 which encodes a mutant polypeptide of colicin Ia, and a mutant plasmid. After that, the gene of SEQ ID NO.26 or SEQ ID NO.28 is inserted into the mutant plasmid after the codon of 1626 of gene of mutant polypeptide of colicin Ia, obtaining two recombinant plasmids pCHCEB 11 (shown in FIG. 1) and pCHCEB22 (shown in FIG. 2) for the novel polypeptide against tumor caused by EB virus. Sequences of 6 pairs of oligonucleotide primers are shown in SEQ ID NO.11-22, which are designed for the preparation of gene encoding the antibody against EB virus in the recombinant plasmid. The recombination plasmid is transfected into the engineering bacteria of *E. coli* BL21(DE3) (purchased from Novagen Corp.) to prepare the polypeptide. The polypeptides obtained are shown in SEQ ID NO.25 (hereinafter referred to as "novel anti-tumor polypeptide 1") and SEQ ID NO.27 (hereinafter referred to as "novel anti-tumor polypeptide 2") in the sequence list.

The process of double-strand oligonucleotide site-directed mutagenesis follows the Strategene QuickChang Site-Directed Mutagenesis Kit (catalog#200518).

1. Preparation of reactant for site-directed mutagenesis:
   5 μl 10× buffer
   2 μl (10 ng) original plasmid pSELECT™-1 which carries genes of polypeptide of wild-type of colicin Ia and Immunity protein.
   1.25 μl (125 ng) 5'-3' oligonucleotide primer designed
   1.25 μl (125 ng) 3'-5' oligonucleotide primer designed
   1 μl dNTP
   double-distilled water 50 μl
   1 μl pfu
   (provided by the Kit except the plasmid, primers and double-distilled water)

2. PCR amplification, amplification condition: 25 cycles of denaturation at 95° C. for 35 seconds, anneal at 53° C. for 70 seconds, and extension at 68° C. for 17 minutes;

3. 1 μl endonuclease Dpn 1 is added to digest parental DNA chain (37° C., 1 hour), 1 μl reactant and 50 μl XL1-Blue competent cell are incubated together on ice for 30 minute, after a heat shock at 42° C. for 45 second, incubated in ice for 2 minute;

4. 0.5 ml cultivation medium NZY is added, shaking at 37° C. and 220 rpm for 1 hour. 50-100 μl reactant is plated (LB medium plus 1% agar and 50 μg/ml ampicillin, overnight at 37° C.);

5. Colony is picked up after 18 hours. Plasmid is extracted, sequenced, confirming that the mutation is successful;

6. The 50 ng recombination plasmid obtained finally by mutation at multiple sites is incubated with 40 μl E. coli BL-21(DE3) competent cells on ice for 5 minute, heat shocked at 42° C. for 30 second, and incubated in ice for 2 minute. 160 μl cultivation medium SOC from Novagen crop. is added, and plated after shaking at 37° C. and 220 rpm for 1 hour (LB medium plus 1% agar and 50 μg/ml ampicillin, overnight at 37° C.).

7. Single colony is picked up for amplification, 8-16 liters FB medium, 250 rpm, 30° C. for 4-5 hours, heat shocked at 42° C. and 250 rpm for 30 minute, and at 37° C. for 2 hours. The bacterium is precipitated by centrifugation at 6000 g and 4° C. for 20 minute. 50 mM borate buffer (2 mM EDTA+2 mM DTT) at 4° C. and 50-80 ml bacterium suspension is added with 0.2M PMSF 250 ml and treated with ultrasonication (4° C., 400W, 2 minutes). Bacterium debris is high speed centrifugated (4° C., 75,000 g, 90 minutes). The supernatant is added with 5 million units of streptomycin sulphate to precipitate DNA. After precipitation by centrifugation at 15000 g and 4° C. for 10 minutes, the supernatant is dialysed overnight in dialysis bag of molecular weight 15,000 in 50 mM borate buffer at 4° C. After precipitation by centrifugation at 15000 g and 4° C. for 10 minutes again, the supernatant is loaded on a CM ion-exchange column. The column is eluted using a gradient of 0.1-0.3 M NaCl+50 mM borate buffer, obtaining the recombinant anti-tumor polypeptide.

Sequences of primers designed for site-directed mutagenesis are as follows:

```
                                                           SEQ ID NO. 1
oligonucleotide primer 5'-3' designed for mutation of G11A in gene of colicin:
cgt att aca aat ccc GCA gca gaa tcg ctg ggg, SEQ ID NO. 2
oligonucleotide primer 3'-5' designed for mutation of G11A in gene of colicin:
ccc cag cga ttc tgc TGC ggg att tgt aat acg, SEQ ID NO. 3
oligonucleotide primer 5'-3' designed for mutation of H22G in gene of colicin:
gat tca gat ggc GGT aaa tta tgg gtg, SEQ ID NO. 4
oligonucleotide primer 3'-5' designed for mutation of H22G in gene of colicin:
cac cca taa ttt ACC gcc atc tga atc, SEQ ID NO. 5
oligonucleotide primer 5'-3' designed for mutation of A26G in gene of colicin:
gaaa ttatgGGTgt tgatatttat, SEQ ID NO. 6
oligonucleotide primer 3'-5' designed for mutation of A26G in gene of colicin:
ataaatatacaacACCcataatttc, SEQ ID NO. 7
oligonucleotide primer 5'-3' designed for mutation of V31L in gene of colicin:
gt tgatatttat CTC aaccctc cacgtgtc, SEQ ID NO. 8
oligonucleotide primer 3'-5' designed for mutation of V31L in gene of colicin:
gacacgtggagggttGAGataaatatcaac, SEQ ID NO. 9
oligonucleotide primer 5'-3' designed for mutation of H40D in gene of colicin:
cgtgtcga tgtctttGATggtaccccgc ctgcat, SEQ ID NO. 10
oligonucleotide primer 3'-5' designed for mutation of H40D in gene of colicin:
atgcaggcggggtaccATCaaagacatcgacacg, SEQ ID NO. 11
primer 5'-3' for gene of V_HCDR1 in recombination plasmid pCHCEB11:
gcg aat aag ttc tgg ggt att TCC TTC GGT ATG CAT TGG GTG CGTCAGtaa ata aaa tat aag aca ggc, SEQ ID NO. 12
primer 3'-5' for gene of V_HCDR1 in recombination plasmid pCHCEB11:
gcc tgt ctt ata ttt tat tta CTG ACG CAC CCA ATG CAT ACC GAA GGA aat acc cca gaa ctt att cgc, SEQ ID NO. 13
primer 5'-3' for gene of V_HFR_2 in recombination plasmid pCHCEB11:
```

-continued ggt atg cat tgg gtg cgt cag GCC CCC GAG AAA GGT CTG GAG TGG GTG GCC taa ata aaa tat aag aca ggc, SEQ ID NO. 14
primer 3'-5' for gene of V$_H$FR$_2$ in recombination plasmid pCHCEB11:
gcc tgt ctt ata ttt tat tta GGC CAC CCA CTC CAG ACCT TTT CTC GGG GGC ctg acg cac cca atg cat acc, SEQ ID NO. 15
primer 5'-3' for gene of (Rev)V$_l$CDR3 in recombination plasmid pCHCEB11:
aaa ggt ctg gag tgg gtg gcc ACC TAC CCC TAC TCC TAC GGT CAG GGT taa ata aaa tat aag aca ggc, SEQ ID NO. 16
primer 3'-5' for gene of (Rev)V$_L$CDR3 in recombination plasmid pCHCEB11:
gcc tgt ctt ata ttt tat tta ACC CTG ACC GTA GGA GTA GGG GGT ggc cac cca ctc cag acc ttt, SEQ ID NO.17
primer 5'-3' for gene of V$_H$CDR1 in recombination plasmid pCHCEB22:
gcg aat aag ttc tgg ggt att TCC TTC GGT ATG CAT TGG GTG CGT CAG taa ata aaa tat aag aca ggc, SEQ ID NO. 18
primer 3'-5' for gene of V$_H$CDR1 in recombination plasmid pCHCEB22:
gcc tgt ctt ata ttt tat tta CTG ACG CAC CCA ATG CAT ACC GAA GGA aat acc cca gaa ctt att cgc, SEQ ID NO. 19
primer 5'-3' for gene of V$_H$FR$_2$ in recombination plasmid pCHCEB22:
ggt atg cat tgg gtg cgt cag GCC CCC GAG AAA GGT CTG GAG TGG GTG GCC taa ataaaa tat aag aca ggc, SEQ ID NO. 20
primer 3'-5' for gene of V$_H$FR$_2$ in recombination plasmid pCHCEB22:
gcc tgt ctt ata ttt tat tta GGC CAC CCA CTC CAG ACCT TTT CTC GGG GGC ctg acg cac cca atg cat acc, SEQ ID NO. 21
primer 5'-3' for gene of V$_L$CDR3 in recombination plasmid pCHCEB22:
aaa ggt ctg gag tgg gtg gcc GGT CAG GGT TAC TCC TAC CCC TAC ACC taa ata aaa tat aag aca ggc, SEQ ID NO. 22
primer 3'-5' for gene of V$_L$CDR3 in recombination plasmid pCHCEB22:
gcc tgt ctt ata ttt tat tta GGT GTA GGG GTA GGA GTA ACC CTG ACC ggc cac cca ctc cag acc ttt,

EXAMPLE 2

Observation of Immune Effect of Novel Anti-tumor Polypeptides Prepared from Recombination Plasmid pCHCEB11 and pCHCEB22

Mice are immunized with the novel anti-tumor polypeptide 1 and the novel anti-tumor polypeptide 2 prepared from the recombination plasmid pCHCEB11 and pCHCEB22 obtained in Example 1, and the anti-tumor polypeptide 1 and the anti-tumor polypeptide 2 from the former invention owned by inventor (ZL200410081446.8). Each protein described above is mixed with adjuvant. The priming dose and the boost dose are one intraperitoneal injection of 50 μg (0.5 ml) each mouse, five injections with 2 weeks interval totally. Serum titer is determined by indirect ELISA method. The titer of mice immunized with the novel anti-tumor polypeptide 1 and 2 prepared by the present invention range from $10^{-3}$ to le, while the titer of mice immunized with the anti-tumor polypeptide 1 and anti-tumor polypeptide 2 range from $10^{-4}$ to $10^{-5}$.

It can be seen that the possibility of hypersensitive reaction induced by the novel anti-tumor polypeptide of the present invention is 1 order to 2 orders of magnitude lower than the possibility of hypersensitive reaction induced by anti-tumor polypeptide comprising wild-type colicin Ia.

EXAMPLE 3

Experiment of Low Sensitization Effect of the Mutant Polypeptide of Colicin Ia which Forms Novel Anti-tumor Polypeptide The mutant plasmid for mutant polypeptide of colicin Ia (which is mutated at amino acid residues of G11A, H22G, A26G, V31L, and H40D in peptide chain of aqueous channel domain) of Example 1 is operably linked to pheromone AgrD1(YSTCDFIM) of *S. aurous* at N-terminus or C-terminus of the mutant polypeptide, obtaining two antibacterial polypeptides. The polypeptide obtained by the linkage of AgrD1 at carboxyl terminus of the mutant colicin Ia is named as polypeptide 1 against *S. aurous*, and the polypeptide obtained by the linkage of AgrD1 at amino terminus of the mutant colicin Ia is named as polypeptide 1 against *Pseudomonas aeruginosa*. Plasmid for wild-type colicin Ia is linked at amino terminus to pheromone AgrD1(YSTCDFIM) of *S. aurous*, obtaining polypeptide 2 against *Pseudomonas aeruginosa*.

Experiment 1

A batch of Kunming mice are intraperitoneally injected with lethal dose of MRSA (ATCC BAA42), and are grouped randomly into (1) control group, (2) group of ampicillin, (3) group of polypeptide against *S. aurous*, (4) group of polypeptide 1 against *S. aurous*. Each group consists of 10 mice.
Treating method:
One hour after intraperitoneal injection of lethal dose of MRSA (ATCC BAA42):
control group: injected with 0.5 ml 0.3 M NaCl+50 mM borate buffer via tail vein once;
group of ampicillin: injected with ampicillin of 2.5 mg/kg via tail vein once;
group of polypeptide against *S. aurous*: injected with polypeptide against *S. aurous* owned by the inventor (ZL 01128836.1) of 6 mg/kg via tail vein once;
group of polypeptide 1 against *S. aurous*: injected with polypeptide 1 against *S. aurous* of 6 mg/kg via tail vein once;
Result: Mice in the control group and the group of ampicillin are all dead in two days. 85% mice in the group of polypeptide against *S. aurous* and the group of polypeptide 1 against *S. aurous* survive.

Experiment 2

14 days after experiment 1, a new batch of Kunming mice are grouped into a control group and a group of ampicillin. The survived mice from the group of polypeptide against *S. aurous* and the group of polypeptide 1 against *S. aurous* are grouped into a group of polypeptide against *S. aurous* and a group of polypeptide 1 against *S. aurous* to repeat the experiment described above. Mice in the control group and the group of ampicillin are all dead in two days. 75% mice in the group of polypeptide against *S. aurous* survive, and 90% mice in the group of polypeptide 1 against *S. aurous* survive.

Experiment 3

Figure 3:
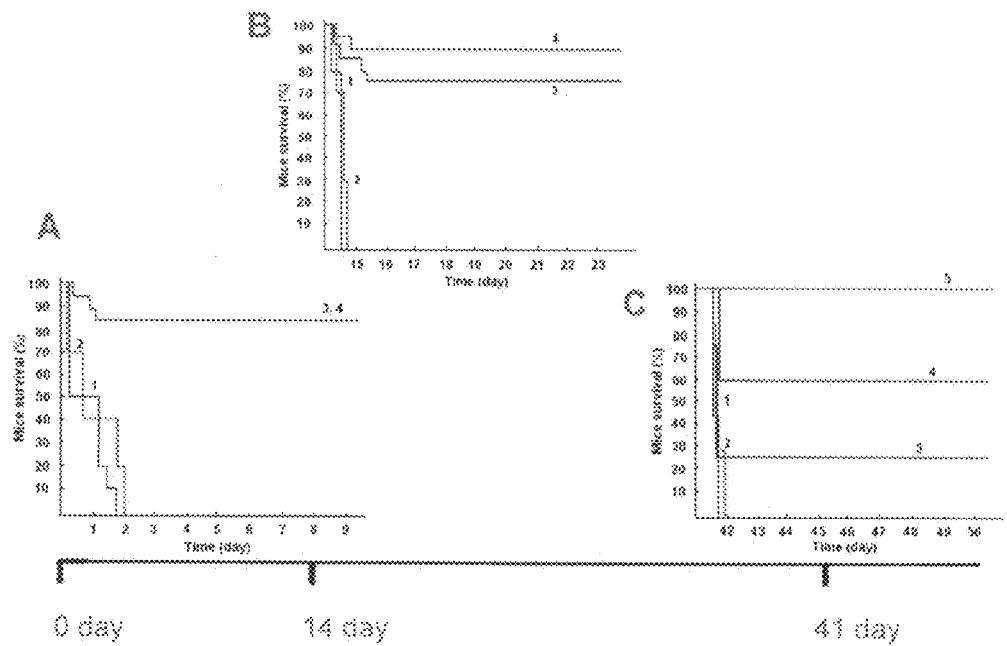
FIG. 3. The experiment 1 of sensitization effect of the mutant polypeptide of colicin Ia.

41 days after experiment 1, a new batch of Kunming mice are grouped into a control group, a group of levofloxacin, and a group of ceftriaxone sodium. The survived mice from the group of polypeptide against *S. aurous* and the group of polypeptide 1 against *S. aurous* are grouped into a group of polypeptide 2 against *Pseudomonas aeruginosa*, and a group of polypeptide 1 against *Pseudomonas aeruginosa*.
Mice are intraperitoneally injected with of lethal dose of multi-drug resistance *Pseudomonas aeruginosa* (clinical isolates 13578 from Department of Experimental Medicine, West China Hospital of Sichuan University). After one hour,
the control group are injected with 0.5 ml 0.3 M NaCl+50 mM borate buffer via tail vein once;
the group of levofloxacin are injected with levofloxacin of 5 mg/kg via tail vein once;
the group of ceftriaxone sodium are injected with ceftriaxone sodium of 30 mg/kg via tail vein once;
the group of polypeptide 2 against *Pseudomonas aeruginosa* are injected with the polypeptide 1 against *Pseudomonas aeruginosa* of 8 mg/kg via tail vein once;
Mice in the control group and the group of levofloxacin are all dead in a day. 25% mice in the group of ceftriaxone sodium survive. 60% mice in the group of polypeptide 2 against *Pseudomonas aeruginosa* survive. All of the mice in the group of polypeptide 1 against *Pseudomonas aeruginosa* survive. It is demonstrated that the antibody of host interfere with the killing effect of the mutant polypeptide lower than with that of wild-type polypeptide.
See FIG. 3.
At week 1, week 2 and week 7 of the experiment, serum of survived mice from the group of polypeptide against *S. aurous*/group of polypeptide 2 against *Pseudomonas aeruginosa*, and the group of polypeptide 1 against *S. aurous*/group of polypeptide 1 against *Pseudomonas aeruginosa* is assayed by indirect ELISA method to detect the antibody in blood. Wells of enzyme label plate are coated with wilt-type colicin Ia and the mutant polypeptide of colicin Ia, 100 ng/well. The first antibodies are serums of survived mice from the group of polypeptide against *S. aurous*/group of polypeptide 2 against *Pseudomonas aeruginosa*, and the group of polypeptide 1 against *S. aurous*/group of polypeptide 1 against *Pseudomonas aeruginosa*. The second antibody is goat anti mouse labeled antibody. The first antibody of negative control is 5% milk-PBS. The results of 1:50,000 titer are as follows (see FIG. 4):

| | A (group of polypeptide against *S. aurous*/ polypeptide 2 against *Pseudomonas aeruginosa*) | B (group of polypeptide 1 against group of *S. aurous*/ group of polypeptide 1 against *Pseudomonas aeruginosa* |
|---|---|---|
| 1 (Week 1) | 0.914 | 0.254 |
| 2 (Week 2) | 1.623 | 0.598 |
| 3 (Week 7) | 2.911 | 1.41 |
| 4 (controll) | 0.065 | 0.069 |

It is demonstrated that the possibility of host's hypersensitive reaction induced by the mutant polypeptide of colicin Ia prepared by the present invention is lower than the possibility of host's hypersensitive reaction induced by wild-type colicin Ia.

EXAMPLE 4

In vitro Killing Effect of the Novel Anti-tumor Polypeptide to Burkitt's Lymphoma Caused by EB Virus EBV positive cell strain and EBV negative cell strain is standard cell strain from ATCC, USA.
Cell cultivation: 0.1 ml suspension of revived Raji cell is added slowly into 3 ml 1640 liquid medium (plus 10% serum) in a culture dish (dilution rate, 1:30), mixed, and cultured in a 37° C. incubator with $CO_2$. The EBV positive cell strain is ATCC CCL-86 (a standard Burkitt's lymphoma cell used in laboratories in the world, Raji cell, isolated from a 12 year old Africa boys in 1963).
The test cells are grouped into 3 groups.
The group 1 is a blank group, which is added with a preservation solution (10 mMPB+0.2M NaCl phosphate buffer (pH7.4)) without the anti-tumor polypeptide.

The group 2 is added with 200 m/ml the novel anti-tumor polypeptide 1 (plasmid pCHCEB11, preservation solution, 10 mMPB+0.2M NaCl phosphate buffer, pH7.4).

The group 3 is added with 200 m/ml the novel anti-tumor polypeptide 2 (plasmid pCHCEB22, preservation solution, 10 mMPB+0.2M NaCl phosphate buffer, pH7.4).

After cultivation for 24 hours, the culture dish is added with the treating agents described above. 72 hours after the addition of the treating agents, the culture dish is added with 20 μl of 100 μMol propidium iodide (PI), and observed under microscope 10 minutes later. The result shows that the cells of blank group grow well, and the most of cells in the group of novel anti-tumor polypeptide 1 are stained red by PI, showing that cell membrane is destroyed by the anti-tumor polypeptide, which leads to the death of tumor cells. Comparing the number of dead cells, the effect of novel anti-tumor polypeptide 2 is not so well among two novel anti-tumor polypeptides, see FIG. 5.

EXAMPLE 5

Observation of Multi-fluorescence Staining for the in vitro Killing Effect of the Novel Anti-tumor Polypeptide to Cells of Burkitt's Lymphoma Caused by EB Virus and other Tumor Cells The condition of cell cultivation is the same as Example 2. Three cell strains are used in the experiment: EB-virus positive cell strain: ATCC CCL-86(Raji cell, Burkitt's lymphoma cell); ATCC CRL-2230, a strain of malignant lymphosarcoma cell from a 46 year old man with AIDS, which is positive for EB-virus and Kaposi sarcoma virus; EB-virus negative cell strain: ATCC CRL-1648(CA-46, a cell isolated from ascitic fluid of patient of American Burkitt's lymphoma).

Each strain is group into 2 test group. The group 1 is added with a preservation solution (10 mMPB+0.2M NaCl phosphate buffer (pH7.4)) without the novel anti-tumor polypeptide. The group 2 is added with 200 m/ml the novel anti-tumor polypeptide 1 (plasmid pCHCEB11), the preservation solution is 10 mMPB+0.2M NaCl phosphate buffer, pH7.4.

After cultivation for 24 hours, the culture dish is added with the treating agents of the group described above. 72 hours after the addition of the treating agents, the culture dish is added with two types of fluorescent dyes, i.e. 20 μl of 50 μMol FITC and 20 μl of 50 uMol Rodamin-123, and observed under microscope Olympus IX-71 10 minutes later.

The result shows that the strain of EBV negative tumor cell grows well after the treatment of the novel anti-tumor polypeptide 1, and the most cells from every strain of EBV positive tumor cells appear the disappearance of mitochondrion and nucleus, is swelling and necrosis, most of them are dead. Apparently, compared with the PI stain experiment of Example 4, the result from the experiment of multi-fluorescence staining shows more clearly the powerful killing effect of the novel anti-tumor polypeptide 1 against EB virus positive tumor cell, see FIG. 6.

EBV negative tumor cells grow well, which means that the novel anti-tumor polypeptide does not attack the cell without surface antigen of EB virus in cell membrane. It is suggested that the novel anti-tumor polypeptide of the present invention has an ideal targeting specificity and safety.

EXAMPLE 6

Killing Effect of the Novel Anti-tumor Polypeptide to Solid Tumor Grown in Naked Mice Planted with Cells of Burkitt's Lymphoma Caused by EB Virus SCID immunodeficient mice are purchased from Shanghai Laboratory Animal Center, Chinese Academy of Sciences. The mice are fed follow the standard feeding requirements. Water, bedding straw and feedstuff are all sterilized by high temperature or UV light. The mice are fed one weed under relative aseptic condition, and used in the inoculation experiment if there's no abnormality.

Cell suspensions of Raji (ATCC CCL-86) and 1648 (ATCC CRL-1648) in exponential phase are collected in 50 ml centrifuge tubes, centrifuged at 4° C. The supernatant is then discarded. The cells are resuspended in 1640 liquid culture medium (plus calf serum) to $1.0 \times 10^7$ cells/ml. The mice are injected subcutaneously with 0.1 ml of cell suspension of Raji at left axillary, and with 0.1 ml of cell suspension of 1648 (ATCC CRL-1648) at right axillary.

3-4 days after injection, the tumor grows into about 2×2 mm. The mice bearing the tumor are group into:

(group A) the preservation solution (10 mM PBS+0.2M NaCl phosphate buffer (pH7.4)) without the anti-tumor polypeptide, as control group;

(group B) the novel anti-tumor polypeptide 1 (plasmid pCHCEB11), as treating group, 300 μg/mouse/day (calculated as 25 g), for 20 days continuously.

Ten mice of each group are injected subcutaneously 0.5 ml twice a day for 20 days continuously. The behavior of mice is observed and documented every day. The size of tumor is determined and photographed every two days.

The result (see FIG. 7) shows that the growth of tumor in group B of the novel anti-tumor polypeptide is inhibited significantly, wherein tumors in 7 mice disappear, and tumors in the other 3 mice are smaller clearly than that of control group. The novel anti-tumor polypeptide is effective to inhibit the growth of solid tumor in mice caused by EBV positive cells of lymphosarcoma. But the novel anti-tumor polypeptide is ineffective to inhibit the growth of solid tumor in mice caused by EBV negative cells of lymphosarcoma.

EXAMPLE 7

Pathological Observation of In Vivo Experiment of Tumor Elimination

Histopathology observation of tumors: Mice are sacrificed at the end of the experiment of Example 6. Tumors are extracted, fixed in 10% formalin. The paraffin slices are HE stained and observed under routine optical microscopy.

Observed under the microscopy, the solid tumors from mice of control group is proliferating vigorously; the cells of EBV positive solid tumors from mice of group of the novel anti-tumor polypeptide shrink remarkably. Most of the cell masses in the section are necrotic tumor cells, and a large amount of peritumoral lymphocytic infiltration is observed. The histopathology result suggests that during the treatment of 20 days, the novel anti-tumor polypeptide killed nearly all of the tumor cells in the solid tumor (see FIG. 8, D).

The invention claimed is:

1. A fusion polypeptide against a tumor caused by an EB virus, the fusion polypeptide comprising:
   a mutant polypeptide of colicin Ia or Ib which can form ion channels; and
   a polypeptide of an anti-EB virus antibody or a polypeptide of an anti-EB virus antibody mimetic operably linked with the mutant polypeptide of colicin Ia or Ib which can form ion channels,
   wherein the mutant polypeptide of colicin Ia or Ib which can form ion channels includes a mutation of amino acid residues G11A, H22G, A26G, V31L, and 40D of wild-type colicin Ia or Ib,
   wherein the polypeptide of the anti-EB virus antibody has an amino acid sequence identical to an amino acid sequence of a polypeptide of a monoclonal antibody secreted by hybridoma of ATCC HB-168.

2. The fusion polypeptide against the tumor caused by the EB virus according to claim 1, wherein the polypeptide of the antibody mimetic is a connected peptide of a CDR1 region of heavy chain, a linking peptide segment of a CDR1-CDR2 of a heavy chain and a CDR3 of a light chain of the anti-EB virus antibody.

3. The fusion polypeptide against the tumor caused by the EB virus according to claim 2, wherein the mutant polypeptide of colicin Ia or Ib which can form ion channels is obtained by mutation of the wild-type colicin Ia.

4. The fusion polypeptide against the tumor caused by the EB virus according to claim 3, wherein the fusion polypeptide against the tumor caused by the EB virus has the amino acid sequence as set forth in SEQ ID NO. 29.

5. A gene encoding the fusion polypeptide against the tumor caused by the EB virus of claim 1.

6. The gene according to claim 5, wherein the gene comprises the nucleotide sequence as set forth in SEQ ID NO. 30.

7. A recombination plasmid comprising the gene of claim 5.

8. A preparation method for the fusion polypeptide against the tumor caused by the EB virus, comprising steps of:
  transforming the recombination plasmid of claim 7 into an expression system for expression, and
  isolating the polypeptide expressed, which polypeptide is formed by an operable linkage of a mutant polypeptide of colicin Ia or Ib which can form ion channels with a polypeptide of an anti-EB virus antibody or a polypeptide of an anti-EB virus antibody mimetic,
  wherein the mutant polypeptide of colicin Ia or Ib which can form ion channels is obtained by mutation of amino acid residues of G11A, H22G, A26G, V31L, and H40D of wild-type colicin Ia or Ib,
  wherein the polypeptide of the anti-EB virus antibody has an amino acid sequence identical to an amino acid sequence of a polypeptide of a monoclonal antibody secreted by hybridoma of ATCC HB-168.

9. A mutant polypeptide of colicin Ia comprising the amino acid sequence set forth in SEQ ID NO. 24.

10. A gene encoding the mutant polypeptide of colicin Ia of claim 9.

* * * * *

UNITED STATES PATENT AND TRADEMARK OFFICE
CERTIFICATE OF CORRECTION

PATENT NO.       : 8,883,161 B2                                    Page 1 of 1
APPLICATION NO.  : 13/516605
DATED            : November 11, 2014
INVENTOR(S)      : Qiu It is certified that error appears in the above-identified patent and that said Letters Patent is hereby corrected as shown below:

In the Specification

In Column 1, Line 7, delete "filed" and insert -- field --, therefor.

In Column 7, Line 18, delete "crop." and insert -- crop --, therefor.

In Column 10, Line 49, delete "to le," and insert -- to $10^{-4}$, --, therefor.

In Column 12, Line 3, delete "polypeptide 2" and insert -- polypeptide 1 --, therefor.

In Column 12, Line 5, delete "once;" and insert -- once. --, therefor.

In Column 12, Line 41, delete "(controll)" and insert -- (control) --, therefor.

In Column 13, Line 1, delete "200 m/ml" and insert -- 200 μg/ml --, therefor.

In Column 13, Line 4, delete "200 m/ml" and insert -- 200 μg/ml --, therefor.

In Column 13, Line 43, delete "200 m/ml" and insert -- 200 μg/ml --, therefor.

In Column 13, Line 51, delete "50 uMol" and insert -- 50 μMol --, therefor.

In the Claims

In Column 39, Line 62, in Claim 1, delete "40D" and insert -- H40D --, therefor.

Signed and Sealed this
Thirty-first Day of March, 2015

Michelle K. Lee
*Director of the United States Patent and Trademark Office*

SEQUENCE LISTING

<160> NUMBER OF SEQ ID NOS: 32

<210> SEQ ID NO 1
<211> LENGTH: 33
<212> TYPE: DNA
<213> ORGANISM: Artificial Sequence
<220> FEATURE:
<223> OTHER INFORMATION: oligonucleotide primer 5'-3'designed for
      mutation of G11A in gene of colicin

<400> SEQUENCE: 1
cgtattacaa atcccgcagc agaatcgctg ggg                             33

<210> SEQ ID NO 2
<211> LENGTH: 33
<212> TYPE: DNA
<213> ORGANISM: Artificial Sequence
<220> FEATURE:
<223> OTHER INFORMATION: oligonucleotide primer 3'-5' designed for
      mutation of G11A in gene of colicin

<400> SEQUENCE: 2
ccccagcgat tctgctgcgg gatttgtaat acg                             33

<210> SEQ ID NO 3
<211> LENGTH: 27
<212> TYPE: DNA
<213> ORGANISM: Artificial Sequence
<220> FEATURE:
<223> OTHER INFORMATION: oligonucleotide primer 5'-3' designed for
      mutation of H22G in gene of colicin

<400> SEQUENCE: 3
gattcagatg gcggtaaatt atgggtg                                    27

<210> SEQ ID NO 4
<211> LENGTH: 27
<212> TYPE: DNA
<213> ORGANISM: Artificial Sequence
<220> FEATURE:
<223> OTHER INFORMATION: oligonucleotide primer 3'-5' designed for
      mutation of H22G in gene of colicin

<400> SEQUENCE: 4
gattcagatg gcaccaaatt atgggtg                                    27

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer 5'-3' designed for
      mutation of A26G in gene of colicin

<400> SEQUENCE: 5
gaaattatgg gtgttgatat ttat                                       24

<210> SEQ ID NO 6
<211> LENGTH: 24
<212> TYPE: DNA
<213> ORGANISM: Artificial Sequence
<220> FEATURE:
<223> OTHER INFORMATION: oligonucleotide primer 3'-5' designed for
      mutation of A26G in gene of colicin

<400> SEQUENCE: 6
gaaattatga ccgttgatat ttat                                       24

<210> SEQ ID NO 7
<211> LENGTH: 30
<212> TYPE: DNA
<213> ORGANISM: Artificial Sequence
<220> FEATURE:
<223> OTHER INFORMATION: oligonucleotide primer 5'-3' designed for
      mutation of V31L in gene of colicin

<400> SEQUENCE: 7
gttgatattt atctcaaccc tccacgtgtc                                        30

<210> SEQ ID NO 8
<211> LENGTH: 30
<212> TYPE: DNA
<213> ORGANISM: Artificial Sequence
<220> FEATURE:
<223> OTHER INFORMATION: oligonucleotide primer 3'-5' designed for
      mutation of V31L in gene of colicin

<400> SEQUENCE: 8
gacacgtgga gggttgagat aaatatcaac                                        30

<210> SEQ ID NO 9
<211> LENGTH: 34
<212> TYPE: DNA
<213> ORGANISM: Artificial Sequence
<220> FEATURE:
<223> OTHER INFORMATION: oligonucleotide primer 5'-3' designed for
      mutation of H40D in gene of colicin

<400> SEQUENCE: 9
cgtgtcgatg tctttgatgg taccccgcct gcat                                   34

<210> SEQ ID NO 10
<211> LENGTH: 34
<212> TYPE: DNA
<213> ORGANISM: Artificial Sequence
<220> FEATURE:
<223> OTHER INFORMATION: oligonucleotide primer 3'-5' designed for
      mutation of H40D in gene of colicin

<400> SEQUENCE: 10
atgcaggcgg ggtaccatca aagacatcga cacg                                   34

<210> SEQ ID NO 11
<211> LENGTH: 69
<212> TYPE: DNA
<213> ORGANISM: Artificial Sequence
<220> FEATURE:
<223> OTHER INFORMATION: primer 5'-3' for gene of VHCDR1 in
      recombination plasmid pCHCEB11

<400> SEQUENCE: 11
gcgaataagt tctggggtat ttccttcggt atgcattggg tgcgtcagta aataaaatat       60
aagacaggc                                                               69

<210> SEQ ID NO 12
<211> LENGTH: 69
<212> TYPE: DNA
<213> ORGANISM: Artificial Sequence
<220> FEATURE:
<223> OTHER INFORMATION: primer 3'-5' for gene of VHCDR1 in
      recombination plasmid pCHCEB11

<400> SEQUENCE: 12

```
gcctgtctta tattttattt actgacgcac ccaatgcata ccgaaggaaa taccccagaa    60
cttattcgc                                                            69
```

<210> SEQ ID NO 13
<211> LENGTH: 72
<212> TYPE: DNA
<213> ORGANISM: Artificial Sequence
<220> FEATURE:
<223> OTHER INFORMATION: primer 5'-3' for gene of VHFR2 in recombination
      plasmid pCHCEB11

<400> SEQUENCE: 13

```
ggtatgcatt gggtgcgtca ggcccccgag aaaggtctgg agtgggtggc ctaaataaaa    60
tataagacag gc                                                        72
```

<210> SEQ ID NO 14
<211> LENGTH: 73
<212> TYPE: DNA
<213> ORGANISM: Artificial Sequence
<220> FEATURE:
<223> OTHER INFORMATION: primer 3'-5' for gene of VHFR2 in recombination
      plasmid pCHCEB11

<400> SEQUENCE: 14

```
gcctgtctta tattttattt aggccaccca ctccagacct tttctcgggg gcctgacgca    60
cccaatgcat acc                                                       73
```

<210> SEQ ID NO 15
<211> LENGTH: 69
<212> TYPE: DNA
<213> ORGANISM: Artificial Sequence
<220> FEATURE:
<223> OTHER INFORMATION: primer 5'-3' for gene of (Rev)VlCDR3 in
      recombination plasmid pCHCEB11

<400> SEQUENCE: 15

```
aaaggtctgg agtgggtggc cacctacccc tactcctacg gtcagggtta aataaaatat    60
aagacaggc                                                            69
```

<210> SEQ ID NO 16
<211> LENGTH: 66
<212> TYPE: DNA
<213> ORGANISM: Artificial Sequence
<220> FEATURE:
<223> OTHER INFORMATION: primer 3'-5'for gene of (Rev)VLCDR3 in
      recombination plasmid pCHCEB11

<400> SEQUENCE: 16

```
gcctgtctta tattttattt aaccctgacc gtaggagtag ggggtggcca cccactccag    60
acctttt                                                              66
```

<210> SEQ ID NO 17
<211> LENGTH: 69
<212> TYPE: DNA
<213> ORGANISM: Artificial Sequence
<220> FEATURE:
<223> OTHER INFORMATION: primer 5'-3' for gene of VHCDR1 in
      recombination plasmid pCHCEB22

<400> SEQUENCE: 17

```
gcgaataagt tctgggggtat ttccttcggt atgcattggg tgcgtcagta aataaaatat    60
aagacaggc                                                            69
```

<210> SEQ ID NO 18
<211> LENGTH: 69
<212> TYPE: DNA
<213> ORGANISM: Artificial Sequence
<220> FEATURE:
<223> OTHER INFORMATION: primer 3'-5' for gene of VHCDR1 in
      recombination plasmid pCHCEB22

<400> SEQUENCE: 18
gcctgtctta tattttattt actgacgcac ccaatgcata ccgaaggaaa taccccagaa    60
cttattcgc                                                           69

<210> SEQ ID NO 19
<211> LENGTH: 72
<212> TYPE: DNA
<213> ORGANISM: Artificial Sequence
<220> FEATURE:
<223> OTHER INFORMATION: primer 5'-3' for gene of VHFR2 in recombination
      plasmid pCHCEB22

<400> SEQUENCE: 19
ggtatgcatt gggtgcgtca ggcccccgag aaaggtctgg agtgggtggc ctaaataaaa    60
tataagacag gc                                                       72

<210> SEQ ID NO 20
<211> LENGTH: 73
<212> TYPE: DNA
<213> ORGANISM: Artificial Sequence
<220> FEATURE:
<223> OTHER INFORMATION: primer 3'-5' for gene of VHFR2 in recombination
      plasmid pCHCEB22

<400> SEQUENCE: 20
gcctgtctta tattttattt aggccaccca ctccagacct tttctcgggg gcctgacgca    60
cccaatgcat acc                                                      73

<210> SEQ ID NO 21
<211> LENGTH: 69
<212> TYPE: DNA
<213> ORGANISM: Artificial Sequence
<220> FEATURE:
<223> OTHER INFORMATION: primer 5'-3' for gene of VLCDR3 in
      recombination plasmid pCHCEB22

<400> SEQUENCE: 21
aaaggtctgg agtgggtggc cggtcagggt tactcctacc cctacaccta ataaaatat    60 aagacaggc                                                           69

<210> SEQ ID NO 22
<211> LENGTH: 69
<212> TYPE: DNA
<213> ORGANISM: Artificial Sequence
<220> FEATURE:
<223> OTHER INFORMATION: primer 3'-5' for gene of VLCDR3 in
      recombination plasmid pCHCEB22

<400> SEQUENCE: 22
gcctgtctta tattttattt aggtgtaggg gtaggagtaa ccctgaccgg ccacccactc    60
cagacctt                                                            69

<210> SEQ ID NO 23
<211> LENGTH: 1878
<212> TYPE: DNA

<213> ORGANISM: Artificial Sequence
<220> FEATURE:
<223> OTHER INFORMATION: The gene encoding the mutant polypeptide of colicin Ia

<400> SEQUENCE: 23

```
atgtctgacc ctgtacgtat tacaaatccc gcagcagaat cgctggggta tgattcagat      60
ggcggtgaaa ttatgggtgt tgatatttat ctcaaccctc cacgtgtcga tgtctttgat     120
ggtaccccgc ctgcatggag ttccttcggg aacaaaacca tctggggcgg aaacgagtgg     180
gttgatgatt ccccaacccg aagtgatatc gaaaaaaggg acaaggaaat cacagcgtac     240
aaaaacacgc tcagcgcgca gcagaaagag aatgagaata gcgtactgaa gccggaaaa      300
cgcctctctg cggcgattgc tgcaagggaa aaagatgaaa acacactgaa aacactccgt     360
gccggaaacg cagatgccgc tgatattaca cgacaggagt tcagactcct gcaggcagag     420
ctgagagaat acggattccg tactgaaatc gccggatatg acgccctccg gctgcataca     480
gagagccgga tgctgtttgc tgatgctgat tctcttcgta tatctccccg ggaggccagg     540
tcgttaatcg aacaggctga aaacggcag aaggatgcgc agaacgcaga caagaaggcc      600
gctgatatgc ttgctgaata cgagcgcaga aaaggtattc tggacacccg gttgtcagag     660
ctggaaaaaa atggcggggc agcccttgcc gttcttgatg cacaacaggc ccgtctgctc     720
gggcagcaga cacggaatga cagggccatt tcagaggccc ggaataaact cagttcagtg     780
acggaatcgc ttaacacggc ccgtaatgca ttaaccagag ctgaacaaca gctgacgcaa     840
cagaaaaaca cgcctgacgg caaaacgata gtttcccctg aaaaattccc ggggcgttca     900
tcaacaaatc attctattgt tgtgagcggt gatccgagat ttgccggtac gataaaaatc     960
acaaccagcg cagtcatcga taaccgtgca aacctgaatt atcttctgag ccattccggt    1020
ctggactata aacgcaatat tctgaatgac cggaatccgg tggtgacaga ggatgtggaa    1080
ggtgacaaga aaatttataa tgctgaagtt gctgaatggg ataagttacg gcaaagattg    1140
cttgatgcca gaaataaaat cacctctgct gaatctgcgg taaattcggc gagaaataac    1200
ctcagtgcca gaacaaatga gcaaaagcat gcaaatgacg ctcttaatgc cctgttgaag    1260
gaaaaagaga atatacgtaa ccagctttcc ggcatcaatc agaagatagc ggaagagaaa    1320
agaaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aagatcgtg cagcgattgc cgcagcccctt    1560
gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtatt                                                 1878
```

<210> SEQ ID NO 24
<211> LENGTH: 625
<212> TYPE: PRT
<213> ORGANISM: Artificial Sequence
<220> FEATURE:
<223> OTHER INFORMATION: The amino acid sequence of the mutant polypeptide of colicin Ia

<400> SEQUENCE: 24

```
Ser Asp Pro Val Arg Ile Thr Asn Pro Ala Ala Glu Ser Leu Gly Tyr
1               5                   10                  15

Asp Ser Asp Gly Gly Glu Ile Met Gly Val Asp Ile Tyr Leu Asn Pro
            20                  25                  30

Pro Arg Val Asp Val Phe Asp Gly Thr Pro Pro Ala Trp Ser Ser Phe
        35                  40                  45

Gly Asn Lys Thr Ile Trp Gly Gly Asn Glu Trp Val Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
            115                 120                 125

Thr Arg Gln Glu Phe Arg Leu Leu Gln Ala Glu Leu Arg Glu Tyr Gly
            130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
            195                 200                 205

Arg Lys Gly Ile Leu Asp Thr Arg Leu Ser Glu Leu Glu Lys Asn Gly
        210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Thr Asn His Ser
    290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350

Val Val Thr Glu Asp Val Glu Gly Asp Lys Lys Ile Tyr Asn Ala Glu
            355                 360                 365

Val Ala Glu Trp Asp Lys Leu Arg Gln Arg Leu Leu Asp Ala Arg Asn
        370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
```

```
                    405                 410                 415
Leu Leu Lys Glu Lys Glu Asn Ile Arg Asn Gln Leu Ser Gly Ile Asn
            420                 425                 430

Gln Lys Ile Ala Glu Glu Lys Arg Lys Gln Asp Glu Leu Lys Ala Thr
        435                 440                 445

Lys Asp Ala Ile Asn Phe Thr Thr Glu Phe Leu Lys Ser Val Ser Glu
    450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
            485                 490                 495

Glu Lys Tyr Arg Ala Asp Ile Asn Lys Lys Ile Asn Ala Lys Asp Arg
        500                 505                 510

Ala Ala Ile Ala Ala Leu Glu Ser Val Lys Leu Ser Asp Ile Ser
    515                 520                 525

Ser Asn Leu Asn Arg Phe Ser Arg Gly Leu Gly Tyr Ala Gly Lys Phe
530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
    610                 615                 620

Ile
625

<210> SEQ ID NO 25
<211> LENGTH: 28
<212> TYPE: PRT
<213> ORGANISM: Artificial Sequence
<220> FEATURE:
<223> OTHER INFORMATION: The amino acid sequence of the mimetic antibody
      VHCDR1- VHFR2- VLCDR3

<400> SEQUENCE: 25

Ser Phe Gly Met His Trp Val Arg Gln Ala Pro Glu Lys Gly Leu Glu
1               5                   10                  15

Trp Val Ala Gly Gln Gly Tyr Ser Tyr Pro Tyr Thr
            20                  25

<210> SEQ ID NO 26
<211> LENGTH: 84
<212> TYPE: DNA
<213> ORGANISM: Artificial Sequence
<220> FEATURE:
<223> OTHER INFORMATION: The nucleotide sequence encoding the mimetic
      antibody VHCDR1- VHFR2-VLCDR3

<400> SEQUENCE: 26
tccttcggta tgcattgggt gcgtcaggcc cccgagaaag gtctggagtg ggtggccggt    60
cagggttact cctaccccta cacc                                          84

<210> SEQ ID NO 27
<211> LENGTH: 28
```

```
<212> TYPE: PRT
<213> ORGANISM: Artificial Sequence
<220> FEATURE:
<223> OTHER INFORMATION: The amino acid sequence of the mimetic antibody
      VHCDR1- VHFR2- (Rev)VLCDR3

<400> SEQUENCE: 27

Ser Phe Gly Met His Trp Val Arg Gln Ala Pro Glu Lys Gly Leu Glu
1               5                   10                  15

Trp Val Ala Thr Tyr Pro Tyr Ser Tyr Gly Gln Gly
            20                  25

<210> SEQ ID NO 28
<211> LENGTH: 84
<212> TYPE: DNA
<213> ORGANISM: Artificial Sequence
<220> FEATURE:
<223> OTHER INFORMATION: The nucleotide sequence encoding the mimetic
      antibody VHCDR1- VHFR2- (Rev)VLCDR3

<400> SEQUENCE: 28
tccttcggta tgcattgggt gcgtcaggcc cccgagaaag gtctggagtg ggtggccacc    60
tacccctact cctacggtca gggt                                          84

<210> SEQ ID NO 29
<211> LENGTH: 653
<212> TYPE: PRT
<213> ORGANISM: Artificial Sequence
<220> FEATURE:
<223> OTHER INFORMATION: The amino acid sequence 1 of the polypeptide
      against tumor caused by EB virus

<400> SEQUENCE: 29

Ser Asp Pro Val Arg Ile Thr Asn Pro Ala Ala Glu Ser Leu Gly Tyr
1               5                   10                  15

Asp Ser Asp Gly Gly Glu Ile Met Gly Val Asp Ile Tyr Leu Asn Pro
            20                  25                  30

Pro Arg Val Asp Val Phe Asp Gly Thr Pro Pro Ala Trp Ser Ser Phe
        35                  40                  45

Gly Asn Lys Thr Ile Trp Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205
```

```
Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
                260                 265                 270

Ala Glu Gln Gln Leu Thr Gln Gln Lys Asn Thr Pro Asp Gly Lys Thr
                275                 280                 285

Ile Val Ser Pro Glu Lys Phe Pro Gly Arg Ser Ser Thr Asn His Ser
290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
                340                 345                 350

Val Val Thr Glu Asp Val Glu Gly Asp Lys Lys Ile Tyr Asn Ala Glu
                355                 360                 365

Val Ala Glu Trp Asp Lys Leu Arg Gln Arg Leu Leu Asp Ala Arg Asn
370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
                420                 425                 430

Gln Lys Ile Ala Glu Glu Lys Arg Lys Gln Asp Glu Leu Lys Ala Thr
                435                 440                 445

Lys Asp Ala Ile Asn Phe Thr Thr Glu Phe Leu Lys Ser Val Ser Glu
                450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
                500                 505                 510

Ala Ala Ile Ala Ala Ala Leu Glu Ser Val Lys Leu Ser Asp Ile Ser
                515                 520                 525

Ser Asn Leu Asn Arg Phe Ser Arg Gly Leu Gly Tyr Ala Gly Lys Phe
                530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
                580                 585                 590

Ser Ala Leu Gly Ile Ile Gly Tyr Gly Leu Leu Met Ala Val Thr Gly
                595                 600                 605

Ala Leu Ile Asp Glu Ser Leu Val Glu Lys Ala Asn Lys Phe Trp Gly
                610                 615                 620

Ile Ser Phe Gly Met His Trp Val Arg Gln Ala Pro Glu Lys Gly Leu
```

Glu Trp Val Ala Gly Gln Gly Tyr Ser Tyr Pro Tyr Thr
            645                 650

<210> SEQ ID NO 30
<211> LENGTH: 1962
<212> TYPE: DNA
<213> ORGANISM: Artificial Sequence
<220> FEATURE:
<223> OTHER INFORMATION: The nucleotide sequence encoding the amino acid
      sequence 1 of the polypeptide against tumor caused by EB virus

<400> SEQUENCE: 30

```
atgtctgacc ctgtacgtat tacaaatccc gcagcagaat cgctggggta tgattcagat      60
ggcggtgaaa ttatgggtgt tgatatttat ctcaaccctc cacgtgtcga tgtctttgat     120
ggtaccccgc ctgcatggag ttccttcggg aacaaaacca tctggggcgg aaacgagtgg     180
gttgatgatt ccccaacccg aagtgatatc gaaaaaaggg acaaggaaat cacagcgtac     240
aaaaacacgc tcagcgcgca gcagaaagag aatgagaata agcgtactga agccggaaaa     300
cgcctctctg cggcgattgc tgcaagggaa aaagatgaaa acacactgaa acactccgt      360 gccggaaacg cagatgccgc tgatattaca cgacaggagt tcagactcct gcaggcagag     420
ctgagagaat acggattccg tactgaaatc gccggatatg acgccctccg gctgcataca     480
gagagccgga tgctgtttgc tgatgctgat tctcttcgta tatctccccg ggaggccagg     540
tcgttaatcg aacaggctga aaacggcag aaggatgcgc agaacgcaga caagaaggcc     600
gctgatatgc ttgctgaata cgagcgcaga aaggtattc tggacacccg gttgtcagag     660
ctggaaaaaa atggcggggc agcccttgcc gttcttgatg cacaacaggc ccgtctgctc     720
gggcagcaga cacggaatga cagggccatt tcagaggccc ggaataaaact cagttcagtg     780 acggaatcgc ttaacacggc ccgtaatgca ttaaccagag ctgaacaaca gctgacgcaa     840
cagaaaaaca cgcctgacgg caaaacgata gttcccctg aaaaattccc gggcgttca      900 tcaacaaatc attctattgt tgtgagcggt gatccgagat tgccggtac gataaaaatc      960 acaaccagcg cagtcatcga taaccgtgca aacctgaatt atcttctgag ccattccggt    1020
ctggactata aacgcaatat tctgaatgac cggaatccgg tggtgacaga ggatgtggaa    1080
ggtgacaaga aaatttataa tgctgaagtt gctgaatggg ataagttacg gcaaagattg    1140
cttgatgcca gaaataaaat cacctctgct gaatctgcgg taaattcggc gagaaataac    1200
ctcagtgcca gaacaaatga gcaaaagcat gcaaatgacg ctcttaatgc cctgttgaag    1260
gaaaagagaa atatacgtaa ccagctttcc ggcatcaatc agaagatagc ggaagagaaa    1320
agaaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaagtac    1500 cgggctgaca ttaacaaaaa aattaatgca aaagatcgtg cagcgattgc cgcagcccctt    1560 gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtatttc cttcggtatg cattgggtgc gtcaggcccc cgagaaaggt    1920
```

```
ctggagtggg tggccggtca gggttactcc taccccctaca cc                  1962
```

<210> SEQ ID NO 31
<211> LENGTH: 653
<212> TYPE: PRT
<213> ORGANISM: Artificial Sequence
<220> FEATURE:
<223> OTHER INFORMATION: The amino acid sequence 2 of the novel
      polypeptide against tumor caused by EB virus

<400> SEQUENCE: 31

```
Ser Asp Pro Val Arg Ile Thr Asn Pro Ala Glu Ser Leu Gly Tyr
1               5                   10                  15

Asp Ser Asp Gly Gly Glu Ile Met Gly Val Asp Ile Tyr Leu Asn Pro
            20                  25                  30

Pro Arg Val Asp Val Phe Asp Gly Thr Pro Pro Ala Trp Ser Ser Phe
            35                  40                  45

Gly Asn Lys Thr Ile Trp Gly Gly Asn Glu Trp Val Asp Asp Ser Pro
50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
            115                 120                 125

Thr Arg Gln Glu Phe Arg Leu Leu Gln Ala Glu Leu Arg Glu Tyr Gly
130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
            195                 200                 205

Arg Lys Gly Ile Leu Asp Thr Arg Leu Ser Glu Leu Glu Lys Asn Gly
210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
            275                 280                 285

Ile Val Ser Pro Glu Lys Phe Pro Gly Arg Ser Ser Thr Asn His Ser
290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350
```

Val Val Thr Glu Asp Val Glu Gly Asp Lys Lys Ile Tyr Asn Ala Glu
          355                 360                 365

Val Ala Glu Trp Asp Lys Leu Arg Gln Arg Leu Leu Asp Ala Arg Asn
    370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
            420                 425                 430

Gln Lys Ile Ala Glu Glu Lys Arg Lys Gln Asp Glu Leu Lys Ala Thr
        435                 440                 445

Lys Asp Ala Ile Asn Phe Thr Thr Glu Phe Leu Lys Ser Val Ser Glu
    450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
            500                 505                 510

Ala Ala Ile Ala Ala Ala Leu Glu Ser Val Lys Leu Ser Asp Ile Ser
        515                 520                 525

Ser Asn Leu Asn Arg Phe Ser Arg Gly Leu Gly Tyr Ala Gly Lys Phe
    530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
    610                 615                 620

Ile Ser Phe Gly Met His Trp Val Arg Gln Ala Pro Glu Lys Gly Leu
625                 630                 635                 640

Glu Trp Val Ala Thr Tyr Pro Tyr Ser Tyr Gly Gln Gly
                645                 650

<210> SEQ ID NO 32
<211> LENGTH: 1962
<212> TYPE: DNA
<213> ORGANISM: Artificial Sequence
<220> FEATURE:
<223> OTHER INFORMATION: The nucleotide sequence encoding the amino acid
      sequence 2 of the novel polypeptide against tumor caused by EB
      virus

<400> SEQUENCE: 32
atgtctgacc ctgtacgtat tacaaatccc gcagcagaat cgctggggta tgattcagat    60
ggcggtgaaa ttatgggtgt tgatatttat ctcaaccctc cacgtgtcga tgtctttgat   120
ggtaccccgc tgcatggag ttccttcggg aacaaaacca tctggggcgg aaacgagtgg   180
gttgatgatt cccaacccg aagtgatatc gaaaaaggg acaaggaaat cacagcgtac   240
aaaaacacgc tcagcgcgca gcagaaagag aatgagaata gcgtactga agccggaaaa   300

```
cgcctctctg cggcgattgc tgcaagggaa aaagatgaaa acacactgaa aacactccgt    360
gccggaaacg cagatgccgc tgatattaca cgacaggagt tcagactcct gcaggcagag    420
ctgagagaat acggattccg tactgaaatc gccggatatg acgccctccg gctgcataca    480
gagagccgga tgctgtttgc tgatgctgat tctcttcgta tatctccccg ggaggccagg    540
tcgttaatcg aacaggctga aaaacggcag aaggatgcgc agaacgcaga caagaaggcc    600
gctgatatgc ttgctgaata cgagcgcaga aaagtattc tggacacccg gttgtcagag     660
ctggaaaaaa atggcggggc agcccttgcc gttcttgatg cacaacaggc ccgtctgctc    720
gggcagcaga cacggaatga cagggccatt tcagaggccc ggaataaact cagttcagtg    780
acggaatcgc ttaacacggc ccgtaatgca ttaaccagag ctgaacaaca gctgacgcaa    840
cagaaaaaca cgcctgacgg caaaacgata gtttcccctg aaaaattccc ggggcgttca    900
tcaacaaatc attctattgt tgtgagcggt gatccgagat ttgccggtac gataaaaatc    960
acaaccagcg cagtcatcga taaccgtgca aacctgaatt atcttctgag ccattccggt   1020
ctggactata aacgcaatat tctgaatgac cggaatccgg tggtgacaga ggatgtggaa   1080
ggtgacaaga aaatttataa tgctgaagtt gctgaatggg ataagttacg gcaaagattg   1140
cttgatgcca gaaataaaat cacctctgct gaatctgcgg taaattcggc gagaaataac   1200
ctcagtgcca gaacaaatga gcaaaagcat gcaaatgacg ctcttaatgc cctgttgaag   1260
gaaaaagaga atatacgtaa ccagctttcc ggcatcaatc agaagatagc ggaagagaaa   1320
agaaaacagg atgaactgaa ggcaacgaaa gacgcaatta atttcacaac agagttcctg   1380
aaatcagttt cagaaaaata tggtgcaaaa gctgagcagt tagccagaga gatggccggg   1440
caggctaaag ggaagaaaat acgtaatgtt gaagaggcat taaaaacgta tgaaaagtac   1500
cgggctgaca ttaacaaaaa aattaatgca aaagatcgtg cagcgattgc cgcagcccttt  1560 gagtctgtga agctgtctga tatatcgtct aatctgaaca gattcagtcg gggactggga   1620
tatgcaggaa aatttacaag tcttgctgac tggatcactg agtttggtaa ggctgtccgg   1680
acagagaact ggcgtcctct tttttgttaaa acagaaacca tcatagcagg caatgccgca   1740
acggctcttg tggcactggt cttcagtatt cttaccggaa gcgctttagg cattatcggg   1800
tatggtttac tgatggctgt caccggtgcg ctgattgatg aatcgcttgt ggaaaaagcg   1860
aataagttct ggggtatttc cttcggtatg cattgggtgc gtcaggcccc cgagaaaggt   1920
ctggagtggg tggccaccta cccctactcc tacggtcagg gt                      1962
```